(12) United States Patent
Kuchar

(10) Patent No.: US 6,447,730 B1
(45) Date of Patent: *Sep. 10, 2002

(54) MULTI-FUNCTIONAL HOLDER ARTICLE AND METHOD OF USING SAME

(75) Inventor: Michael A. Kuchar, W150 N5304 Badger Dr., Menomonee Falls, WI (US) 53051

(73) Assignee: Michael A. Kuchar, Menomonee Falls, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/480,244

(22) Filed: Jan. 11, 2000

Related U.S. Application Data

(63) Continuation-in-part of application No. 09/053,993, filed on Apr. 2, 1998, now Pat. No. 6,013,230.

(51) Int. Cl.[7] ................................................. B01L 9/00
(52) U.S. Cl. ...................... 422/104; 422/102; 600/573; 248/309.1; 248/311.2; 248/315; 220/737; 220/738; 220/752; 220/754; 220/755; 220/756; 220/757; 220/758; 220/764; 215/395; 215/396
(58) Field of Search ........................... 422/99, 102, 104; 600/573, 574, 580; 248/309.1, 311.2, 312, 312.1, 315; 206/217, 438, 569; 220/737–738, 752, 754–758, 762, 763, 764; 215/395, 396, 398; D24/122, 128, 227

(56) References Cited

U.S. PATENT DOCUMENTS

| | | | |
|---|---|---|---|
| 2,210,972 A | 8/1940 | Christenson | 211/41.2 |
| 2,628,054 A | 9/1953 | Fazakerley | 248/311.2 |
| D304,795 S | 11/1989 | Klopp | D7/70 |
| D306,648 S | 3/1990 | Jones et al. | D24/54 |
| D320,331 S | 10/1991 | Paone | D7/620 |
| 5,096,669 A | 3/1992 | Lauks et al. | 422/61 |
| 5,147,342 A | 9/1992 | Kane et al. | 604/356 |
| 5,165,639 A | 11/1992 | Knuppe | 248/215 |
| 5,174,965 A | 12/1992 | Jones et al. | 422/102 |
| D334,804 S | 4/1993 | Jones et al. | D24/128 |
| D335,179 S | 4/1993 | Jones et al. | D24/128 |
| D335,180 S | 4/1993 | Jones et al. | D24/128 |
| 5,202,094 A | 4/1993 | Jones et al. | 422/102 |
| D335,346 S | 5/1993 | Jones et al. | D24/128 |
| D335,708 S | 5/1993 | Jones et al. | D24/128 |
| 5,316,732 A | 5/1994 | Golukhov et al. | 422/102 |
| 5,342,330 A | 8/1994 | Kane et al. | 604/329 |
| 5,422,076 A | 6/1995 | Jones | 422/102 |
| D364,458 S | 11/1995 | Jones et al. | D24/128 |
| 5,558,840 A | 9/1996 | Jones et al. | 422/104 |
| D376,297 S | 12/1996 | Jacobson | D7/553 |
| 6,013,230 A | * 1/2000 | Kuchar | 422/104 |

* cited by examiner

Primary Examiner—Maureen M. Wallenhorst
(74) Attorney, Agent, or Firm—Reinhart, Boerner, Van Deuren, S.C.

(57) ABSTRACT

An apparatus and method for collecting a biological fluid specimen. The apparatus includes a holder article for a specimen container, wherein the holder article contains a ring which is removably engagable with a specimen container, a connector continuous with the ring, and a grasping portion continuous with the connector. The article can be reconfigured with the grasping portion movable along a longitudinal axis to provide a specimen collection area.

5 Claims, 7 Drawing Sheets

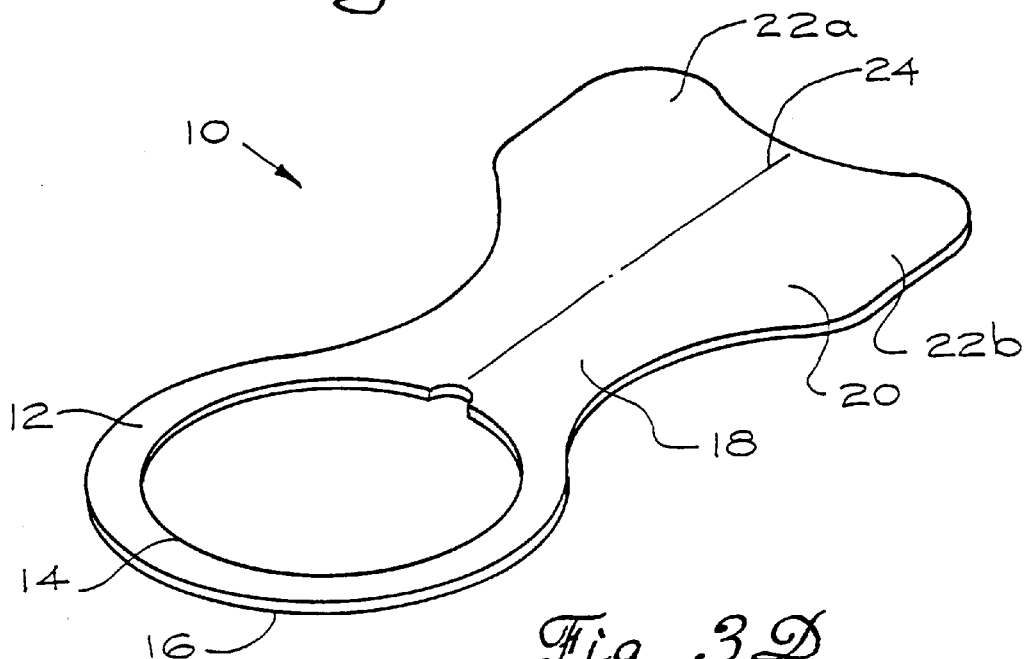
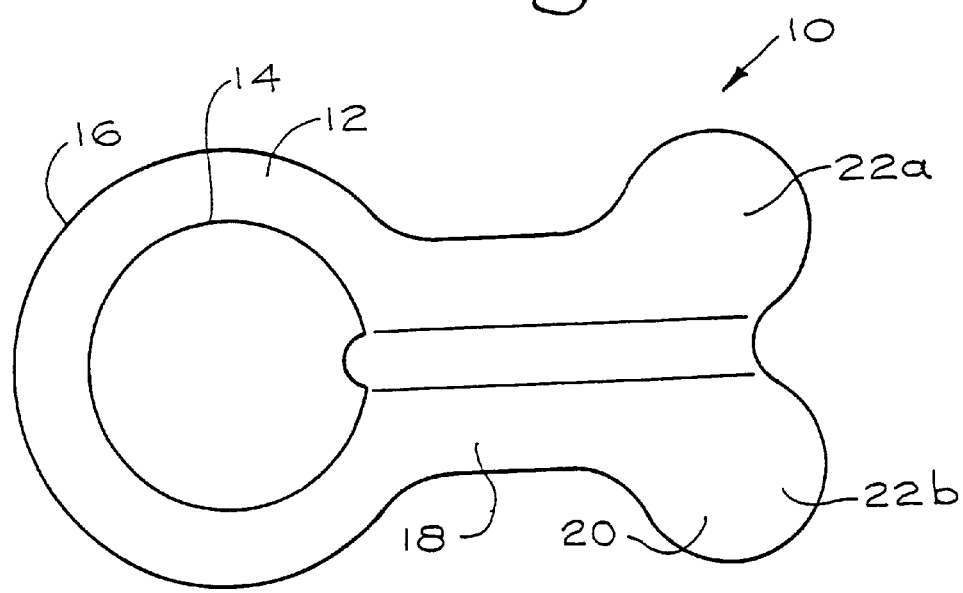

MULTI-FUNCTIONAL HOLDER ARTICLE AND METHOD OF USING SAME

This application is a continuation-in-part of application Ser. No. 09/053,993, filed on Apr. 2, 1998 and now U.S. Pat. No. 6,013,230, issued on Jan. 11, 2000.

BACKGROUND OF THE INVENTION

The present invention relates generally to articles for holding fluid specimen containers and, more particularly but without limitation, is directed toward such articles which can also be used to contain and/or collect errant or misdirected specimen samples.

Over the past decade, there has been an increased need and demand for analysis of various biological specimens, for purposes ranging from pregnancy testing to drug analysis. Considerable time and effort has been expended by way of devising systems and analytic techniques to ensure reliable testing and accurate results. However, relatively little effort has been devoted toward the design and development of articles to conveniently and hygienically collect such specimens. The situation is uniquely illustrated in the context of collecting urine specimens.

Typically, specimen containers and related support devices require that the container and/or device be held by the person rendering the urine specimen. Often times, a difficult situation arises through inadvertent contact with the specimen. The accompanying unpleasantness is not isolated with the specimen provider, but is shared by the health care worker or laboratory technician asked to handle or analyze the urine specimen.

The search for an efficient, economical holder device for specimen containers has been a long-standing concern in the art. Most devices utilize a long handle attached to a ring configuration which engages the specimen container. A problem arises in that the weight of the container and collected specimen poses undue stress and strain on the holder. The result is often an instability which causes errant specimen deposit or, ultimately, spillage of the entire specimen. Examples of such prior art devices are described in U.S. Pat. Nos. Des. 335,708, Des. 306,648, Des. 335,346, Des. 325,180, Des. 335,179, Des. 324,804 and 5,202,094. The last of the aforementioned patents illustrates another shortcoming of the prior art, disclosing a configuration wherein an elongated handle has a hinged connection to a ring structure, thereby introducing yet another source of structural weakness upon specimen deposit.

In summary, a considerable number of drawbacks and problems exist in the art relating to holder devices for specimen containers. There is a need for an improved holder, economically produced, to safely and efficiently collect urine specimens.

OBJECTS OF THE INVENTION

It is an object of this invention to overcome the problems and shortcomings of the prior art, including those described above. It can also be an object of this invention to provide a holder device which functions more broadly to contain, collect and transfer errant or misdirected specimens.

It can be another object of the present invention to provide a one-piece holder which is formed unitarily to impart and maintain structural integrity during use.

It can also be an object of this invention to provide a holder article which inhibits the inadvertent deposit of a specimen on the outside of an intended container.

It can also be an object of this invention to provide a method of using an article, in accordance with this invention, to direct an errant specimen, collect it, then transfer it to an intended container.

It can also be an object of this invention to provide a one-piece holder preform, formed unitarily, which can be reconfigured according to design to assist in specimen collection, such reconfiguration to impart and maintain structural integrity during use.

It can also be an object of the present invention to provide a one-piece holder preform, which can be reconfigured in conjunction an adhesive component to impart and maintain structural integrity during use.

It will be understood by those skilled in the art that one or more aspects of this invention can meet certain objectives, while one or more other aspects can meet certain other objectives. Each objective may not apply equally, in all instances, to every aspect of this invention. As such, the preceding objects—in light of the prior art regarding such holder devices and specimen containers—can be viewed in the alternative with respect to any one aspect of the present invention. Other objects, features and advantages of the present invention will be apparent from the following summary and description of preferred embodiments, and as would be recognized by those skilled in the art having knowledge of specimen collection techniques and the requirements for holder articles as used in the specimen analysis industry. Such objects, features, benefits and advantages will also be apparent from the above as taken in conjunction with the accompanying figures and all reasonable inferences to be drawn therefrom.

SUMMARY OF THE INVENTION

This invention includes a new and/or improved holder article, as well as a method of using the same. The invention overcomes certain well-known problems and deficiencies, including those outlined above, while providing a cost-effective alternative to current devices. As described more fully below, the invention provides an article more user-friendly, but also more considerate and hygienic with respect to downstream health care workers and laboratory technicians.

In part, the present invention is a holder article for a specimen container of the type having an upper opening. The inventive article includes (1) a ring having a width dimension and an interior diametral dimension, with a proximate portion with respect to the user of the article, such ring removably engagable with a specimen container; (2) a connector continuous with the ring and having a width dimension; and (3) a grasping portion continuous with the connector and having opposed lateral sides. The sides of grasping portion 20 can be substantially contiguous with one another or, alternatively, can have a noncontiguous relationship.

In preferred embodiments, the proximate portion of the ring is continuous therealong with the connector. Preferred embodiments can also include a grasping portion that is movable along a longitudinal axis thereof, such that the lateral sides are approachable one to another, resulting with each portion positioned on opposed sides of the plane coaxial with the aforementioned longitudinal axis. In highly preferred embodiments, the connector has a width dimension greater than the interior diametral dimension of the ring. Likewise, in highly preferred embodiments, the connector is substantially non-coplanar with the ring. One or more of such structural features in combination with another provides the inventive holder article a structural stability heretofore unavailable through the prior art.

In part, the present invention also includes a method using a holder for a specimen cup to contain an errant specimen sample. The method includes (1) providing a holder having a ring removably engagable with the cup, a connector continuous with the ring, and a grasping portion continuous with the connector and having opposed lateral side portions; (2) positioning the lateral sides of the grasping portion to provide a conduit along a line defining a longitudinal axis of the grasping portion; and (3) thereby directing an errant specimen sample along the conduit. In preferred embodiments, the lateral side portions are pre-formed to provide such a conduit. In other embodiments, such outer side portions can be moved one toward another to provide the same sort of conduit. Regardless, the conduit is preferably directed toward a specimen collection area.

As discussed more fully above, a ring with a raised interior edge and a downward flange along the outer dimension can assist in removal of an errant specimen from the collection area. A raised edge engaging a specimen cup can also operate as a guard to prevent intake from a specimen first contacting the holder article. In highly preferred embodiments, the raised edge can be configured for threaded engagement with the specimen cup. Such an engagement, alone or together with the aforementioned downward flange, operates to keep an errant specimen from soiling the outside surface of the specimen cup.

Without limitation, the present invention can also be an improvement of prior art holder articles, such an improvement including a connector continuous with both a ring and a grasping portion and configured in conjunction with the ring to provide a specimen collection area. Such an improvement can further include a grasping and support portion substantially co-planar with the ring, having opposed lateral side portions, either contiguous or noncontiguous, positioned such that the grasping portion provides a conduit directed toward the collection area. While preferred embodiments include side portions pre-formed to provide such a conduit, other embodiments include side portions which are approachable one to another to provide the same sort of conduit. Likewise, in preferred embodiments, the ring associated with such an improvement can be configured to facilitate movement of a specimen from the collection area. As described more fully above, such a configuration can include a raised interior edge on the ring and a downward flange continuous with the ring outer dimension, with a trough or channel therebetween.

Various embodiments of the present invention provide a unique functionality. The interior diametral dimension of the aforementioned ring can be defined by a raised edge. Such structure, in combination with a connector non-coplanar with the ring, can provide a specimen collection area. A downward flange continuous with the outer dimension of the ring can serve to prevent inadvertent specimen deposit along the outer container surface and also assist, in a drip-proof fashion, with removal of the specimen from the aforementioned collection area.

BRIEF DESCRIPTION OF THE DRAWINGS

FIG. 3C is a structural variation of the article of FIG. 3A, showing pre-formed elevated lateral side portions 22a and 22b.

FIG. 3D is an elevated perspective view of the article of FIG. 3A.

FIG. 4A is a top view of another holder article, in accordance with this invention.

FIG. 6B is a holder article of the type resulting from the preform of

FIG. 6A reconfigured as described herein.

DESCRIPTION OF THE PREFERRED EMBODIMENTS

Figure 1A:
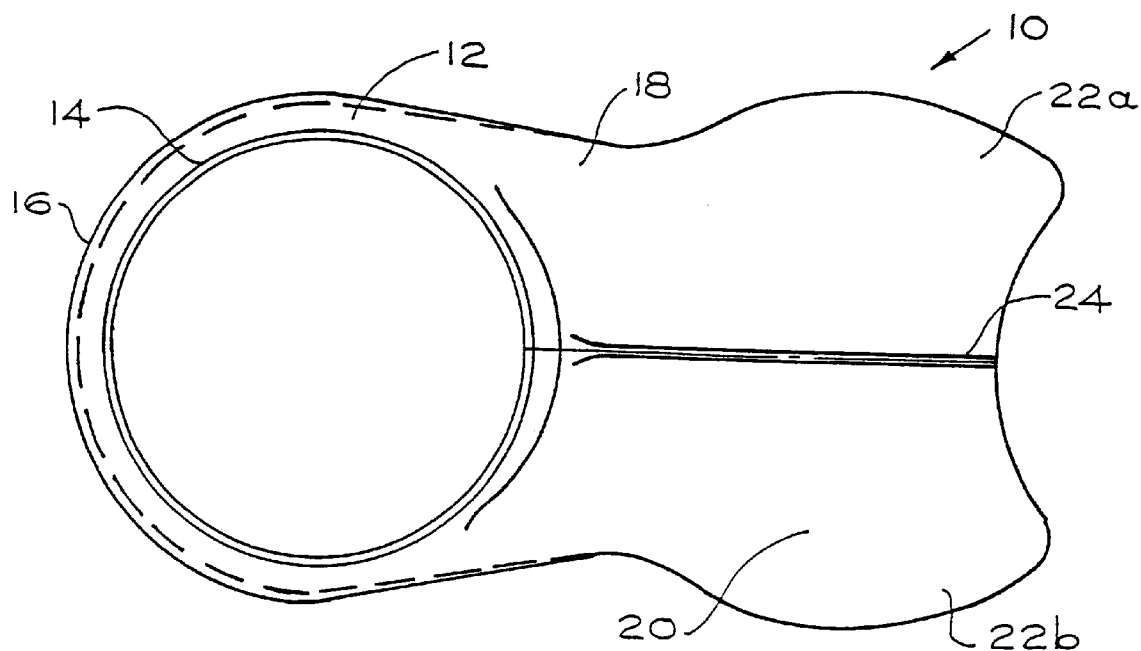
FIG. 1A is a top view of a preferred holder article, in accordance with this invention.
Figure 1B:
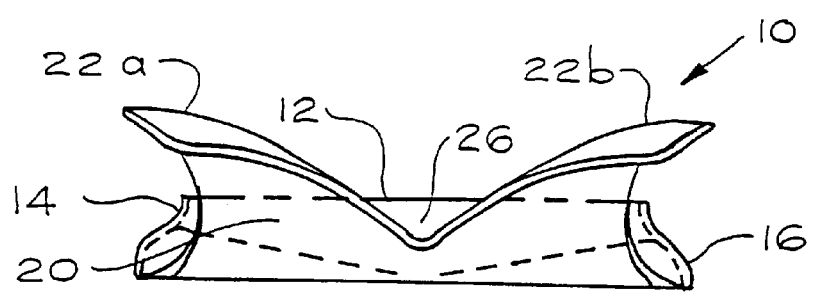
FIG. 1B is a rear view of the article shown in FIG. 1A.
Figure 1C:
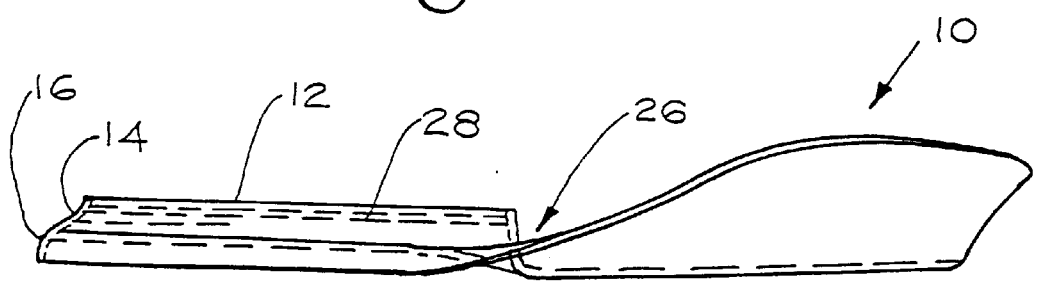
FIG. 1C is a side view of the article shown in FIGS. 1A and 1B.

A preferred embodiment of the present invention is as shown in FIGS. 1A–1C. With reference to FIG. 1A, holder article 10 includes ring 12 continuous with connector 18 which is continuous with grasping portion 20. Ring 12 has an inner diameter 14, which in preferred embodiments is a raised edge, as more clearly in FIG. 1C. Likewise, in preferred embodiments, ring 12 has an outer diameter including downward flange 16, as more clearly shown in FIGS. 1B and 1C. Grasping portion 20 includes opposed lateral side. portions 22a and 22b, respectively, configured about longitudinal axis 24. As more clearly shown in FIG. 1B, the lateral side portions are positioned about longitudinal axis 24 to provide a conduit toward specimen collection area 26. With reference to FIG. 1C, area 26 and ring 12 are configured together to provide a route for specimen evacuation from area 26. While not shown in FIG. 1C, article 10 can be lifted by grasping portion 20 to permit gravity flow of the specimen from collection area 26 toward the distal portion of downward flange 16. As also shown in FIG. 1C, raised edge 14 of ring 12 can be configured with threads 28 for a mating engagement with a specimen container.

While grasping portion 20 of the embodiment shown in FIG. 1A is pre-formed to provide an elevated arrangement of lateral side portions, it should be understood that other embodiments of the present invention provide grasping portion 20 in a substantially planar relationship with connector 18 and ring 12. With such other embodiments, grasping portion 20is movable along a longitudinal axis such that lateral sides 22a and 22b of portion 20 are approachable one to another on opposed sides of the plane coaxial with the longitudinal axis. Movement of the grasping portion in this manner, in accordance with this invention, provides a functional utility comparable to the pre-formed grasping portion shown in FIGS. 1A–1C. Specific reference is made to FIG.

2. Other such embodiments, in accordance with the present invention, are as provided in FIGS. 3A–D and 4A–D, with the structural components thereof enumerated in a manner consistent with those as provided in FIGS. 1A–1C.

Figure 2:
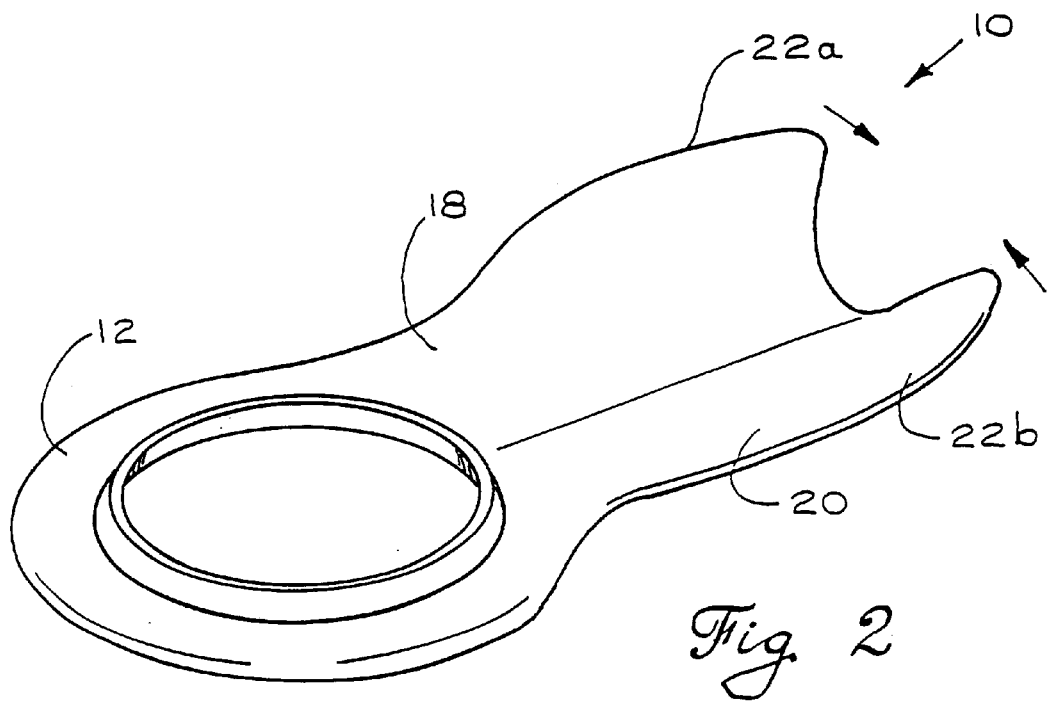
FIG. 2 is an elevated perspective view of a preferred holder article, illustrating movement of the lateral side portions from the horizontal and toward one another.
Figure 3A:
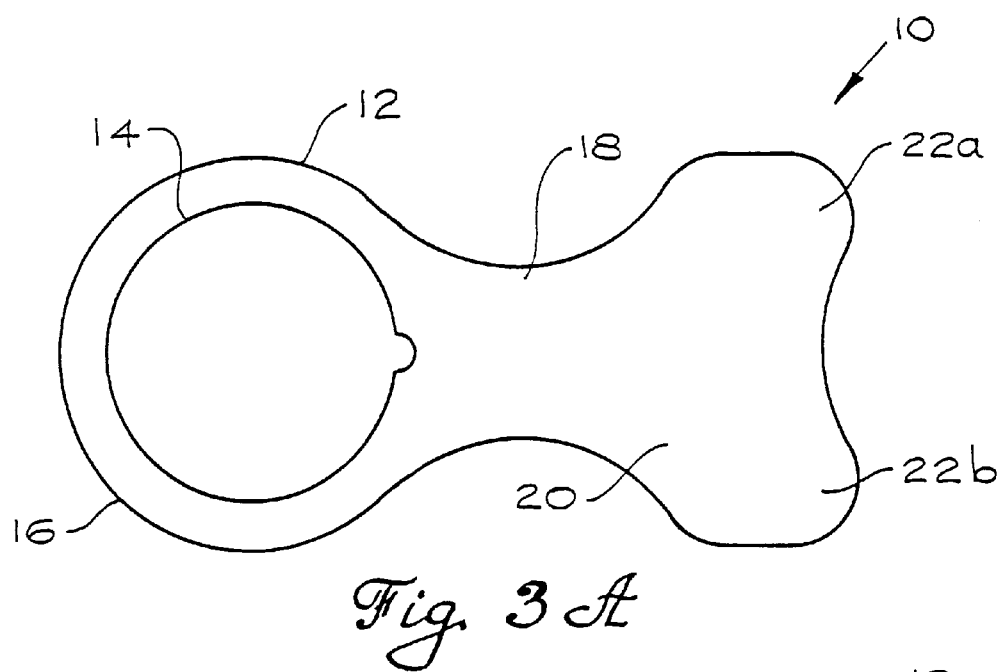
FIG. 3A is a top view of another holder article, in accordance with this invention.
Figure 3B:
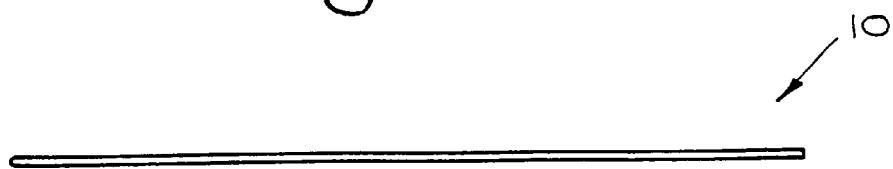
FIG. 3B is a planar side view of the article of FIG. 3A.
Figure 4B:
FIG. 4B is a planar side view of the article of FIG. 4A.
Figure 4C:
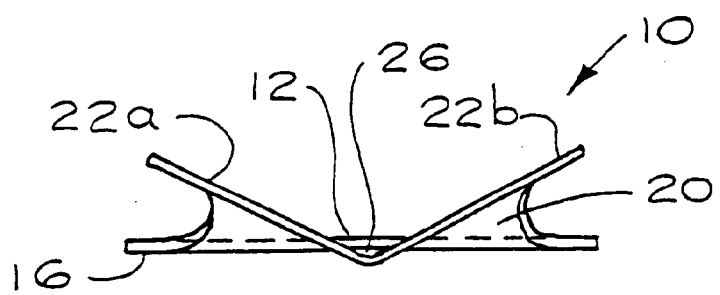
FIG. 4C is a structural variation of the article of FIG. 4A, showing pre-formed elevated lateral side portions 22a and 22b.
Figure 4D:
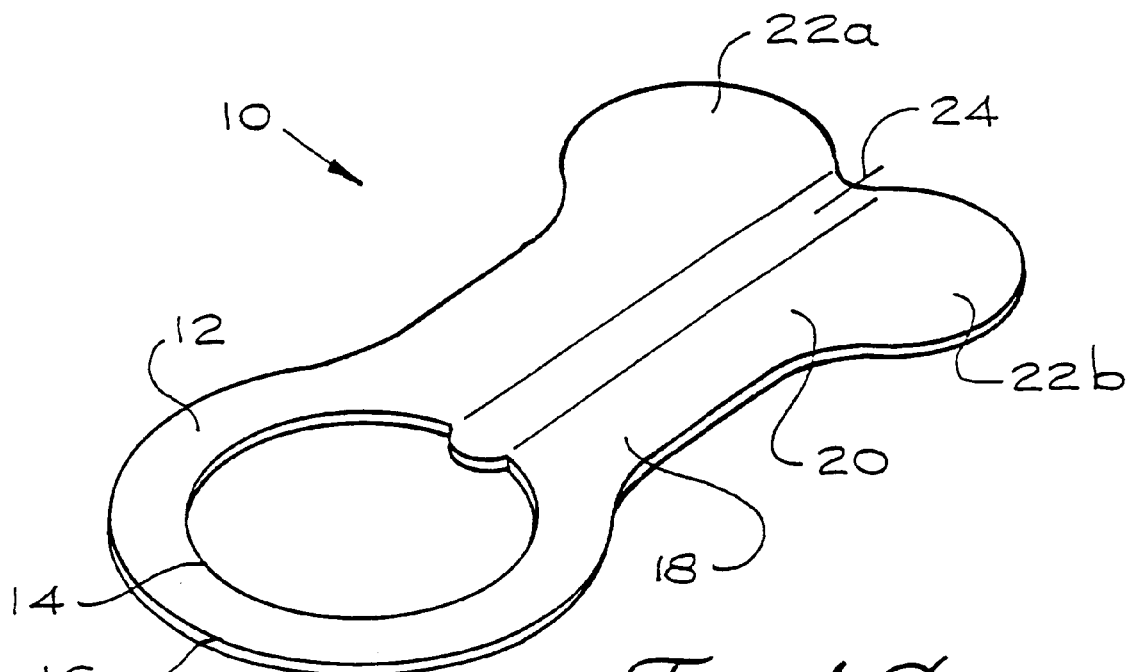
FIG. 4D is an elevated perspective view of the article of FIG. 4A.

Referring again to FIG. 2, holder article 10 is shown with ring 12 having a raised portion along its inner diameter. However, the holder articles of the present invention can be prepared so as to provide a substantially flat side profile perspective. For example, reference is made to FIG. 4B. The holder article of FIG. 5 includes ring 12 with an inner diameter 14 without substantial elevation, so as to provide a planar side view of the sort shown in FIG. 4B. Optionally, the holder article of FIG. 5 can be provided with one or more die cuts or perturbations 30 on inner diameter 14 so as to provide ring 12 the flexibility to accommodate a variety of specimen cup dimensions. Such an article can also include, optionally, score line 32 in one or both of connector 18 and grasping portion 20. In such an embodiment, placement of a specimen cup within ring 12 serves to reconfigure holder article 10, providing a conduit substantially along line 32 and a specimen collection area 26 for errant deposits. As such, the holder article of FIG. 5 can be formed as a substantially planar embodiment, but reconfigured in conjunction with a specimen container to provide a grasping portion, conduit and collection area arrangement similar to that shown more clearly in FIGS. 1B and 1C. Preferred embodiments of the holder article of FIG. 10 are made of various paper and treated paper materials, although a variety of plastics can be used, depending upon material choice and specific product performance requirements.

Figure 6B:
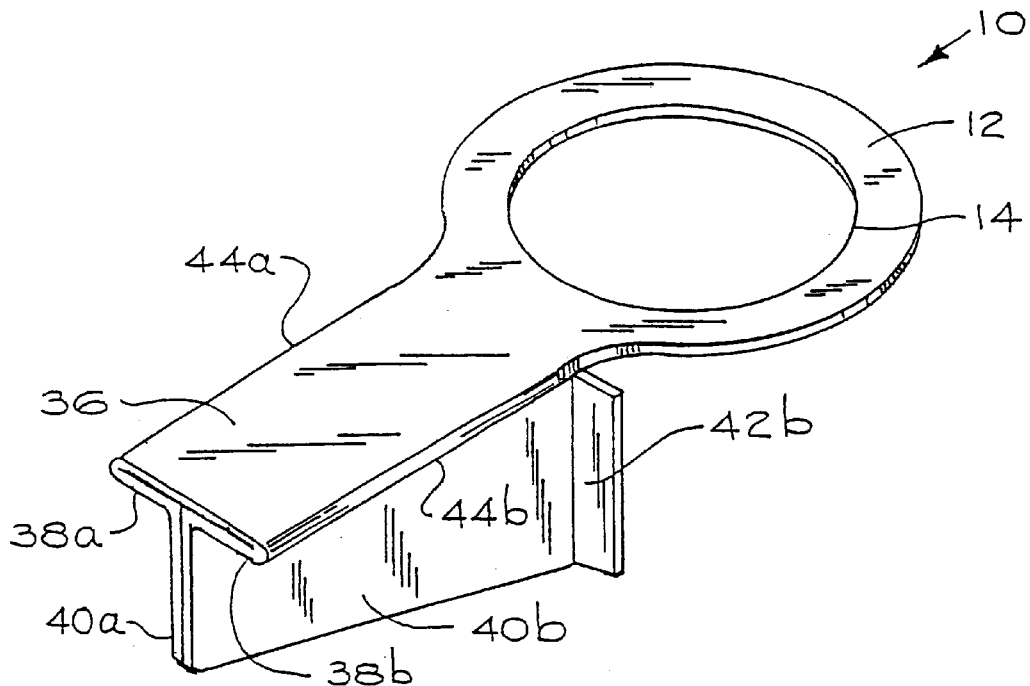
Figure 6A:
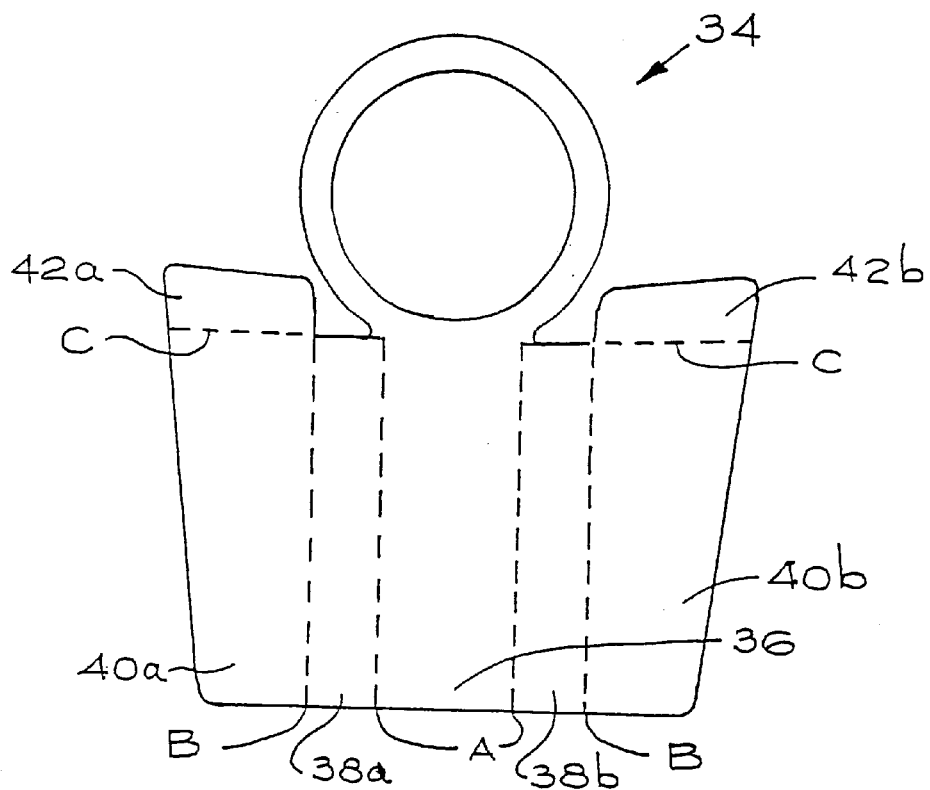
FIG. 6A is a top view of a holder article preform, in accordance with this invention.

Various other alternate holder articles of the present invention can be of the type reconfigured from the corresponding preforms. For example and as shown in FIGS. 6A and 6B, a substantially planar preform 34 can be reconfigured to provide holder article 10. In accordance with this embodiment, portions 38a and 38b can be folded along their respective lines A under portion 36, then folded again along their respective lines B so as to direct portions 40a and 40b adjacent to one another. Optionally, portions 40a and 40b can include anterior portions 42a and 42b, respectively, each of which are foldable along line C. The resulting reconfiguration of preform portion 34 is shown in FIG. 6B. Portions 36, 38a, 38b, 40a and 40b together provide a connector and a grasping portion, both of which are continuous with ring 12. Lateral side portions 44a and 44b of portion 36 are used in conjunction with portions 40a and 40b to support the weight of a specimen container placed in ring 12.

Figure 5:
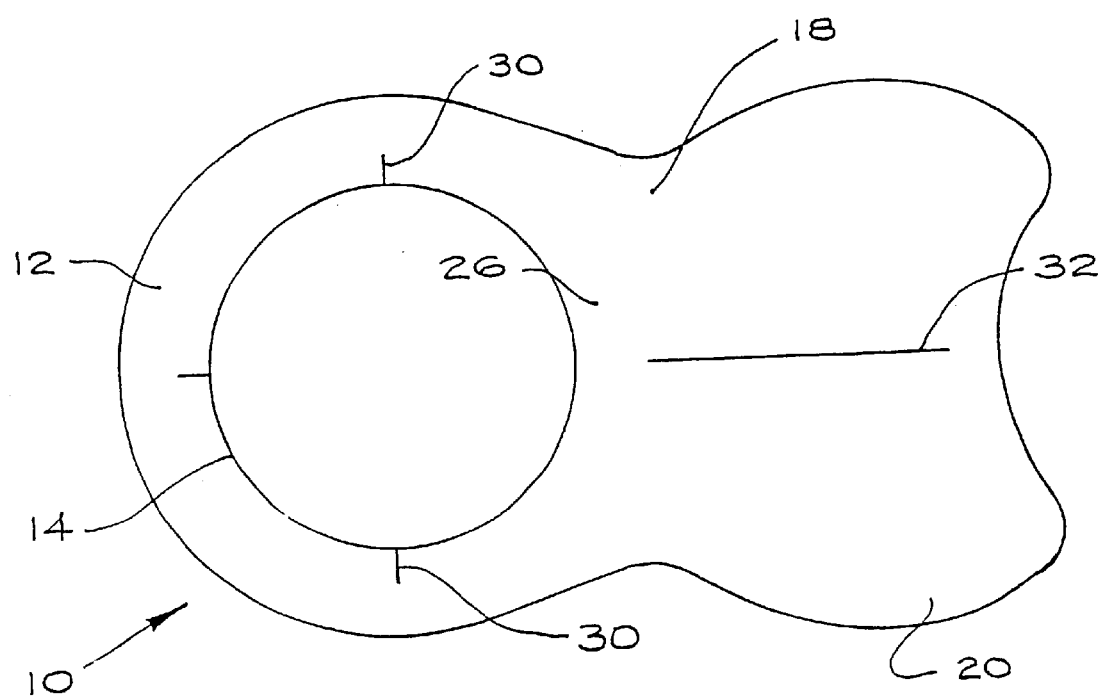
FIG. 5 is a top view of a preferred holder article, in accordance with this invention.

In accordance with this invention, ring 12 can further include one or more die cuts or perturbations along inner ring diameter 14, as otherwise shown in FIG. 5, so as to provide ring 12 the flexibility to accommodate a variety of specimen container dimensions. Portions 40a and/or 40b can further include a contact adhesive to maintain the position of each adjacent one to another upon reconfiguration. Such an adhesive can also promote and maintain structural integrity during use. A variety of mechanical devices such as a clip can, alternatively, also be used to maintain the adjacent placement of portions 40a and 40b.

Figure 7A:
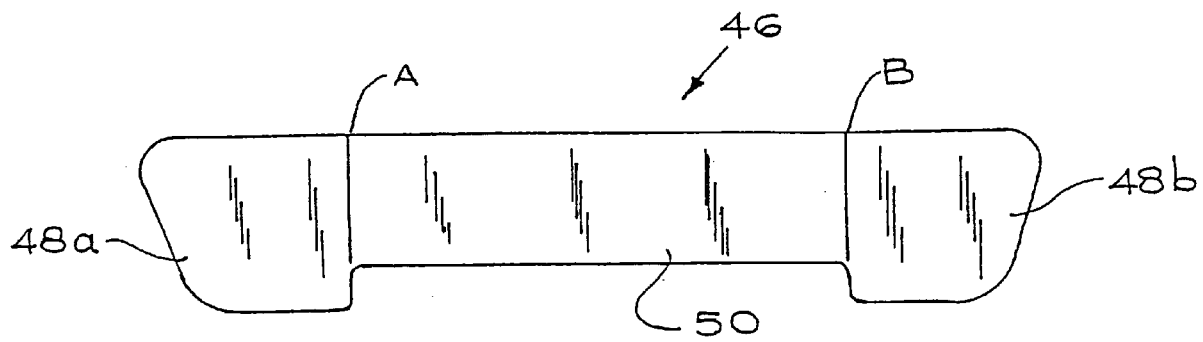
FIG. 7A is a top view of another holder article preform, in accordance with this invention.
Figure 7B:
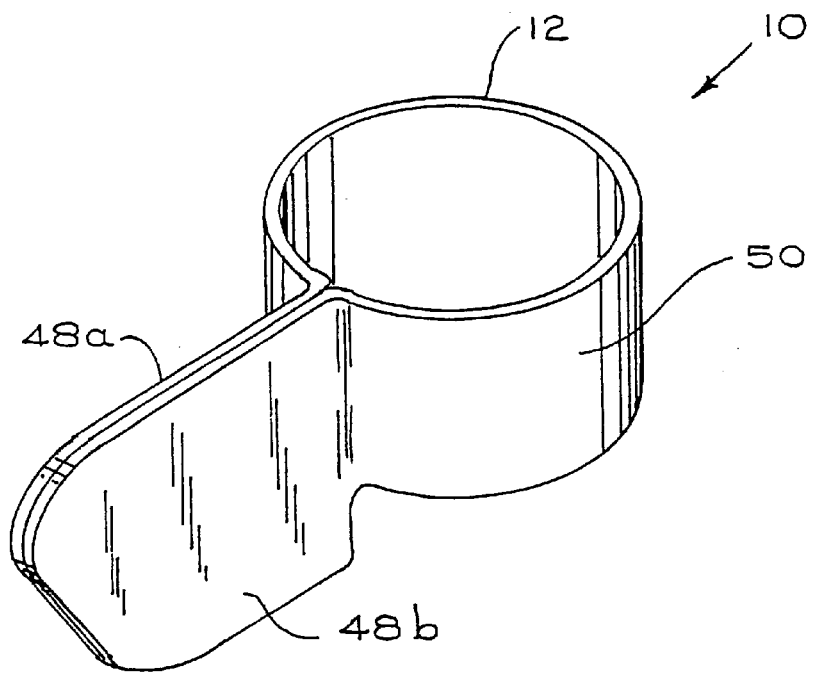
FIG. 7B is a holder article of the type resulting from the preform of FIG. 7A reconfigured as described herein.

Referring to FIGS. 7A and 7B, an alternate embodiment of the present invention is shown by preform portion 46. Portions 48a and 48b are opposed with respect to portion 50, but are approachable one to another upon reconfiguration along lines A and B, respectively, to provide holder article 10, as shown in FIG. 7B. As described more fully above, portions 48a and 48b can be provided with a contact adhesive to further impart and maintain the structural integrity of article 10. As shown in FIG. 7B, portions 48a and 48b align with one another end for end; however, it should be understood that realignment of one portion with respect to another can vary the cross dimension of ring 12 so as to accommodate a variety of specimen containers. Likewise, as discussed more fully above, preform 46 and the corresponding holder article 10 can be prepared from a variety of materials, including paper, coated paper product and various plastic materials.

The holder articles of the present invention can be prepared according to methods and processes well-known to those skilled in the art. Preferred materials include polypropylene and polyethylene, although a variety of materials can be used, including recyclable plastics. Preferred materials include those which have been shown acceptable for the testing and analytic procedures described herein. Using such materials, the present articles can be either cold-formed or heat-formed, depending upon material choice, desired article configuration and specific product parameter and performance requirements. From a manufacturing perspective, reference is again made to FIG. 1A with particular attention to the arc of the outer diameter of ring 12 and the arc of curvature between lateral side portions 22a and 22b. Preferably, from a manufacturing perspective, both arcs have identical curvatures to minimize material waste during sequential formation of such article holders.

While the principles of this invention have been described in connection with specific embodiments, it should be understood clearly that these descriptions, along with the chosen figures and examples, are made only by way of illustration and are not intended to limit the scope of this invention in any manner. For instance, the methods and articles of this invention can be used in the veterinary sciences with equal effect. Likewise, the inventive articles can incorporate structural features to enhance stability, including without limitation ribs or indented areas along a grasping portion of such an article. Other features include those elements to facilitate engagement with a specimen container, from either side of a ring structure. Other advantages and features of this invention will become apparent from the following claims, with the scope thereof determined by usable equivalents, as understood by those skilled in the art.

What is claimed is:

1. A method of reconfiguring a holder for a specimen cup to provide a collection area for an errant specimen sample in the holder, said method comprising:

providing a holder having a ring removably engagable with a specimen cup, a connector continuous with said ring, and a grasping portion continuous with said connector, said holder having a configuration;

placing a specimen cup within said holder ring; and reconfiguring said holder to provide an errant specimen collection area therein which directs an errant specimen towards a specimen cup when engaged by said ring of said holder.

2. The method of claim 1 wherein said holder configuration is substantially planar.

3. The method of claim 1 wherein said ring has perturbations on an inner diameter thereof.

4. The method of claim 1 wherein said holder further includes a score line in at least one of said connector and said grasping portions.

5. The method of claim 4 wherein said holder is reconfigured along said score line.

* * * * *